United States Patent
Okamoto et al.

(10) Patent No.: US 9,395,342 B2
(45) Date of Patent: Jul. 19, 2016

(54) MIST-CONTAINING GAS ANALYSIS DEVICE

(71) Applicant: MITSUBISHI HEAVY INDUSTRIES, LTD., Tokyo (JP)

(72) Inventors: Shinichi Okamoto, Tokyo (JP); Hiromitsu Nagayasu, Tokyo (JP); Takuya Hirata, Tokyo (JP); Masaru Chiyomaru, Tokyo (JP); Hiroshi Tanaka, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 217 days.

(21) Appl. No.: 14/353,298

(22) PCT Filed: Dec. 19, 2012

(86) PCT No.: PCT/JP2012/082883
§ 371 (c)(1),
(2) Date: Apr. 22, 2014

(87) PCT Pub. No.: WO2013/099724
PCT Pub. Date: Jul. 4, 2013

(65) Prior Publication Data
US 2014/0305190 A1    Oct. 16, 2014

(30) Foreign Application Priority Data
Dec. 27, 2011    (JP) .................................. 2011-284659

(51) Int. Cl.
*G01N 33/00* (2006.01)
*B01D 53/14* (2006.01)
(Continued)

(52) U.S. Cl.
CPC ............... *G01N 33/0004* (2013.01); *G01N 7/00* (2013.01); *G01N 15/06* (2013.01); *G01N 21/61* (2013.01);
(Continued)

(58) Field of Classification Search
CPC ............ G01N 33/0004; G01N 1/2247; G01N 2001/2267; G01N 2001/4066; G01N 33/0054; G01N 7/00; G01N 21/61; G01N 25/00; G01N 29/00; G01N 21/3554; G01N 2001/2261; G01N 2015/0026; G01N 15/06; G01N 33/0013; G01N 33/0014; G01N 33/0016; G01N 33/004; Y02C 10/06; B01D 53/1475; B01D 53/62; B01D 2252/102; B01D 2252/204; B01D 2257/504; B01D 2258/0283

See application file for complete search history.

(56) References Cited

U.S. PATENT DOCUMENTS 4,928,015 A * 5/1990 Butler .................... G01J 3/453
                                                     250/339.08
5,187,972 A    2/1993 DeFriez
(Continued)

FOREIGN PATENT DOCUMENTS

JP    58-90144 A    5/1983
JP    2-48856 B2    10/1990
(Continued)

OTHER PUBLICATIONS

Inoue Y et al., "A study of ultrasonic propagation for ultrasonic flow rate measurements", Flow Measurement and Instrumentation, Tokyo, Japan, vol. 19, No. 3-4, Jun. 1, 2008, pp. 223-232.
(Continued)

*Primary Examiner* — John Fitzgerald
*Assistant Examiner* — Michael E Turbyfill
(74) *Attorney, Agent, or Firm* — Westerman, Hattori, Daniels & Adrian, LLP

(57) ABSTRACT

A mist-containing gas analysis device comprises a measuring instrument that measures a pressure, a temperature, a flow rate and water content of a combustion exhaust gas, a collection container, a sampling tube and a guide tube through which the combustion exhaust gas is suctioned by a suction blower, and is sampled and fed into a collection liquid in the collection container, an arithmetic and control device that controls the suction blower such that a suction velocity of the combustion exhaust gas being suctioned by the suction blower is within a predetermined ratio with respect to a combustion exhaust gas flow velocity which is calculated based on the measured values, liquid aliquot taking means for taking an aliquot of the liquid in the collection container, and a measuring device that measures a concentration of the measurement-target substance in the aliquot of the liquid taken by the liquid aliquot taking means.

3 Claims, 3 Drawing Sheets

(51) Int. Cl.
*B01D 53/62* (2006.01)
*G01N 1/22* (2006.01)
*G01N 1/40* (2006.01)
*G01N 7/00* (2006.01)
*G01N 21/61* (2006.01)
*G01N 25/00* (2006.01)
*G01N 29/00* (2006.01)
*G01N 21/3554* (2014.01)
*G01N 15/00* (2006.01)
*G01N 15/06* (2006.01)

(52) U.S. Cl.
CPC ............... *G01N 25/00* (2013.01); *G01N 29/00* (2013.01); *G01N 33/004* (2013.01); *G01N 33/0013* (2013.01); *G01N 33/0014* (2013.01); *G01N 33/0016* (2013.01); *G01N 33/0054* (2013.01); *B01D 53/1475* (2013.01); *B01D 53/62* (2013.01); *B01D 2252/102* (2013.01); *B01D 2252/204* (2013.01); *B01D 2257/504* (2013.01); *B01D 2258/0283* (2013.01); *G01N 1/2247* (2013.01); *G01N 21/3554* (2013.01); *G01N 2001/2261* (2013.01); *G01N 2001/2267* (2013.01); *G01N 2001/4066* (2013.01); *G01N 2015/0026* (2013.01); *Y02C 10/06* (2013.01)

(56) References Cited

U.S. PATENT DOCUMENTS

| | | | |
|---|---|---|---|
| 5,571,946 A | 11/1996 | Koshi et al. | |
| 5,637,809 A | 6/1997 | Traina et al. | |
| 7,771,654 B1 * | 8/2010 | Moore | G01N 33/0031 422/62 |
| 2002/0061594 A1 * | 5/2002 | Itou | C01C 1/024 439/39 |

FOREIGN PATENT DOCUMENTS

| | | | |
|---|---|---|---|
| JP | 6-34499 | A | 2/1994 |
| JP | 7-146227 | A | 6/1995 |
| JP | 10-33938 | A | 2/1998 |
| JP | 10-202053 | A | 8/1998 |
| JP | 2000-206133 | A | 7/2000 |
| JP | 2001-349810 | A | 12/2001 |
| JP | 2003-185478 | A | 7/2003 |
| JP | 2010-256075 | A | 11/2010 |

OTHER PUBLICATIONS

Shirokov I B et al., "Measurement error elimination of matter flow velocity taking into account its physical parameters", Microwave & Telecommutincation Technology, 2005 15th International CRIM EAN Conference Sevastopol, Ukraine Sep. 12-16, 2005, Piscataway, NJ, USA, IEEE, vol. 2, Sep. 12, 2005. pp. 813-814.

"19.3.1.3: Infrared instruments + Chapter 22: Nuclear instrumentation technology" In Instrmentation Reference Bok (Third Edition), Jan. 1, 2003, pp. 417, 517-546.

Extended European Search Report dated Sep. 14, 2015, issued in counterpart European Application No. 12862677.7 (12 pages).

Notification of Transmittal of Translation of the International Preliminary Report on Patentability of International Application No. PCT/JP2012/082883, mailing date of Jul. 10, 2014 (form PCT/IB/338) with forms PCT/ISA/210, PCT/IB/373, PCT/ISA/237 and PCT/ISA/220, w/English translation (21 pages).

"Measuring methods dust concentration in flue gas" (Hai Gas-chu no Dust Nodo no Sokutei Hoho Z8808), Japanese Industrial Standard (JIS), (1995), (26 pages).

* cited by examiner

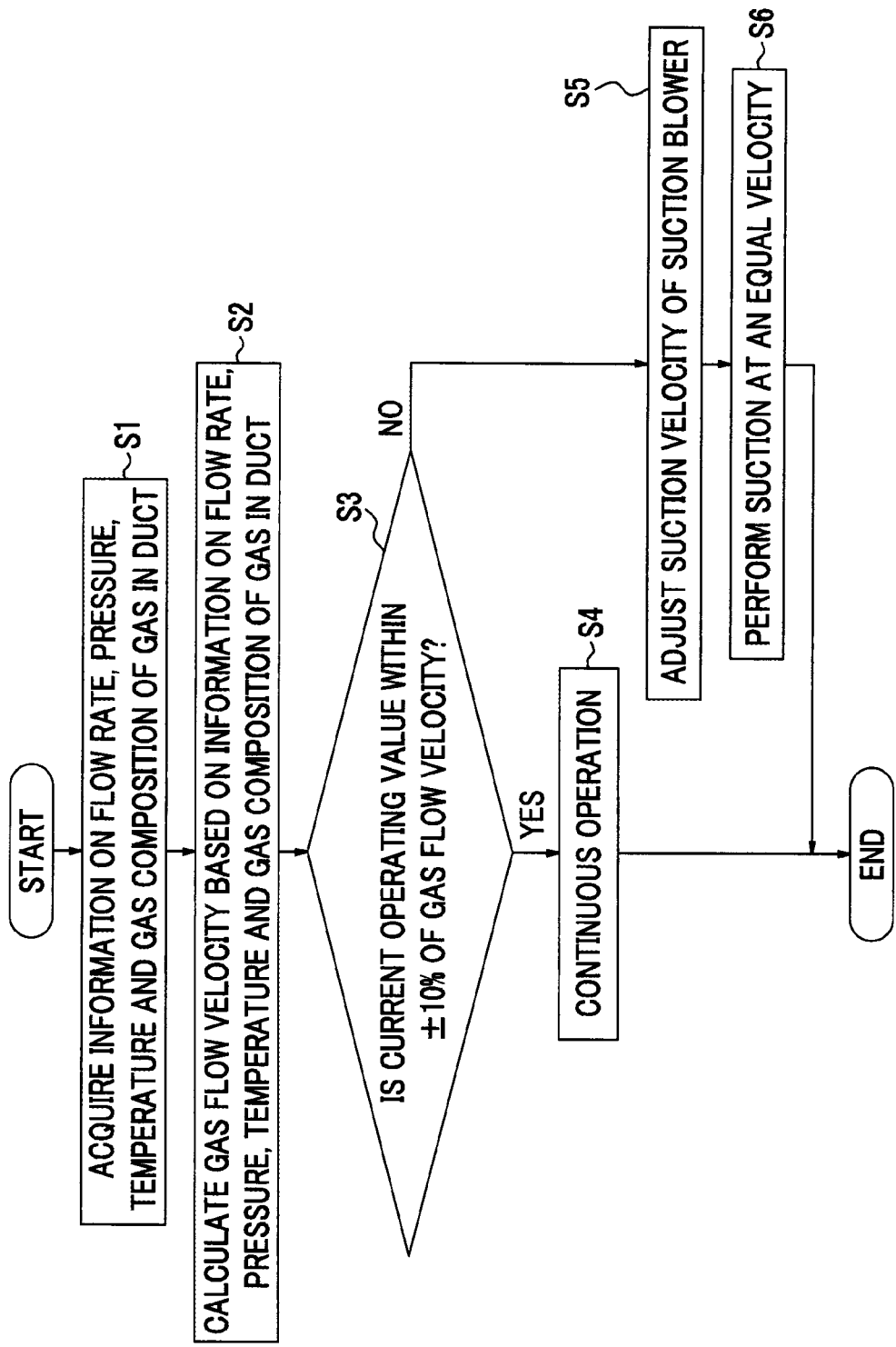

MIST-CONTAINING GAS ANALYSIS DEVICE

TECHNICAL FIELD

The present invention relates to a mist-containing gas analysis device that measures a concentration of a measurement-target substance in a target gas which contains a mist of the measurement-target substance.

BACKGROUND ART

For example, in an exhaust gas processing device equipped with a carbon dioxide recovery device that recovers carbon dioxide in a combustion exhaust gas from a boiler or the like by bringing the combustion exhaust gas into contact with amine-containing absorbing liquid and by absorbing the carbon dioxide in the combustion exhaust gas with the absorbing liquid, a micro amount of amines or ammonia is discharged to the outside together with the combustion exhaust gas from which the carbon dioxide is absorbed and removed, and is discharged by the carbon dioxide recovery device. Accordingly, an operator samples the combustion exhaust gas which is discharged in a state where the carbon dioxide in the combustion exhaust gas absorbed and removed in the carbon dioxide recovery device, and measures concentrations of amines and ammonia (hereinafter, referred to as "amines and the like") which the combustion exhaust gas contains.

CITATION LIST

Patent Literature

[PTL 1] Japanese Unexamined Patent Application Publication No. 58-90144

SUMMARY OF INVENTION

Technical Problem

However, as described above, if the operator samples the combustion exhaust gas and measures concentrations of amines and the like, the operator is required to performs the sampling and an analysis for the measurement. Accordingly, it takes significant effort to perform the measurement.

For example, proposed is a system in which a pitot tube is mounted on a duct, a pressure of an in-duct combustion exhaust gas is measured via the pitot tube, a gas suction velocity of the suction blower connected to a gas sampling tube is adjusted in response to an in-duct combustion exhaust gas flow velocity estimated based on the measured value, a gas suction is performed at a velocity equal to the estimated in-duct combustion exhaust gas velocity and thus, a measurement-target substance in the combustion exhaust gas is accurately measured.

When the measurement-target substance in the combustion exhaust gas is measured in this way, gas flow turbulence in the duct occurs due to the pitot tube, and the in-duct combustion exhaust gas flow velocity cannot be accurately estimated. Accordingly, the gas suction velocity of the suction blower cannot be appropriately adjusted, and the measurement-target substance in the combustion exhaust gas cannot be accurately acquired.

When properties of the in-duct combustion exhaust gas change, for example, when a dust concentration, a mist concentration, a water concentration or the like increases, the substance condenses and clogging occurs in the pitot tube. Accordingly, the gas suction velocity of the suction blower cannot be appropriately adjusted, and the measurement-target substance in the combustion exhaust gas cannot be accurately acquired.

In the exhaust gas processing device equipped with the carbon dioxide recovery device that recovers carbon dioxide in the combustion exhaust gas from a boiler or the like by bringing the combustion exhaust gas into contact with amine-containing absorbing liquid and by absorbing the carbon dioxide in the combustion exhaust gas with the absorbing liquid, the problems occur not only in a case where concentrations of amines and the like in an combustion exhaust gas are measured, but also in a case where a device measures a concentration of a measurement-target substance in a target gas that contains a mist of the measurement-target substance, for example, in a case where the device measures a concentration of a liquid component in outlet gas (for example, a water saturation gas) of a gas-liquid contact device, the same problems can occur similarly to in the initial case.

The present invention is made to solve the problems, and an object of the present invention is to provide a mist-containing gas analysis device that can simply and accurately measure a concentration of a measurement-target substance in a target gas which contains a mist of the measurement-target substance.

Solution to Problem

A mist-containing gas analysis device according to the present invention measures a concentration of a measurement-target substance in a target gas which contains a mist of the measurement-target substance flowing through a duct. The mist-containing gas analysis device includes pressure measuring means for measuring a pressure of the target gas that flows through the duct; temperature measuring means for measuring a temperature of the target gas that flows through the duct; flow rate measuring means for measuring a flow rate of the target gas that flows through the duct by using a radio wave or an ultrasonic wave; water content measuring means for measuring water content in the target gas that flows through the duct by using infrared light; a collection container that contains collection liquid which dissolves the measurement-target substance; target gas sampling means for absorbing the target gas by using suction means and for sampling the target gas; target gas feeding means for feeding the target gas sampled by the target gas sampling means into the collection liquid in the collection container; suction flow rate control means for controlling the suction means in such a manner that a suction velocity of the target gas being suctioned by the suction means is within a predetermined ratio with respect to a target gas flow velocity calculated based on the pressure of the target gas measured by the pressure measuring means, the temperature of the target gas measured by the temperature measuring means, the flow rate of the target gas measured by the flow rate measuring means, and the water content of the target gas measured by the water content measuring means; liquid aliquot taking means for taking an aliquot of the liquid in the collection container; and measuring means for measuring the concentration of the measurement-target substance in the aliquot of the liquid taken by the liquid aliquot taking means.

In the mist-containing gas analysis device according to the present invention, the measurement-target substances are amines and ammonia.

In the mist-containing gas analysis device according to the present invention, the target gas is a combustion exhaust gas from which carbon dioxide is absorbed and removed by the amine-containing absorbing liquid.

Advantageous Effects of Invention

The mist-containing gas analysis device according to the present invention measures a gas flow rate, a pressure, a temperature and water content of the target gas in the duct without causing turbulence of a flow of the target gas, and calculates a flow velocity of the target gas in the duct based on the measured results. The mist-containing gas analysis device controls the suction means in such a manner that a suction velocity of the target gas being suctioned by the suction means is within a predetermined ratio with respect to a flow velocity of the target gas. Accordingly, it is possible to appropriately suck the target gas in the duct at a velocity equal to the flow velocity of the target gas without causing clogging which results from a change in properties of the target gas. Therefore, even though the target gas contains the measurement-target substance not only in a gaseous phase but also in a mist phase, the mist-containing gas analysis device can simply and accurately measure the concentration of the measurement-target substance in the target gas.

BRIEF DESCRIPTION OF DRAWINGS

FIG. 3 is a flow chart illustrating a control of a flow rate of gas being suctioned by a suction blower equipped in the mist-containing gas analysis device in FIG. 1.

DESCRIPTION OF EMBODIMENTS

Embodiments of a mist-containing gas analysis device according to the present invention will be described with reference to the accompanying drawings.

Main Embodiment

A main embodiment of the mist-containing gas analysis device according to the present invention will be described with reference to FIGS. 1 to 3.

Figure 1:
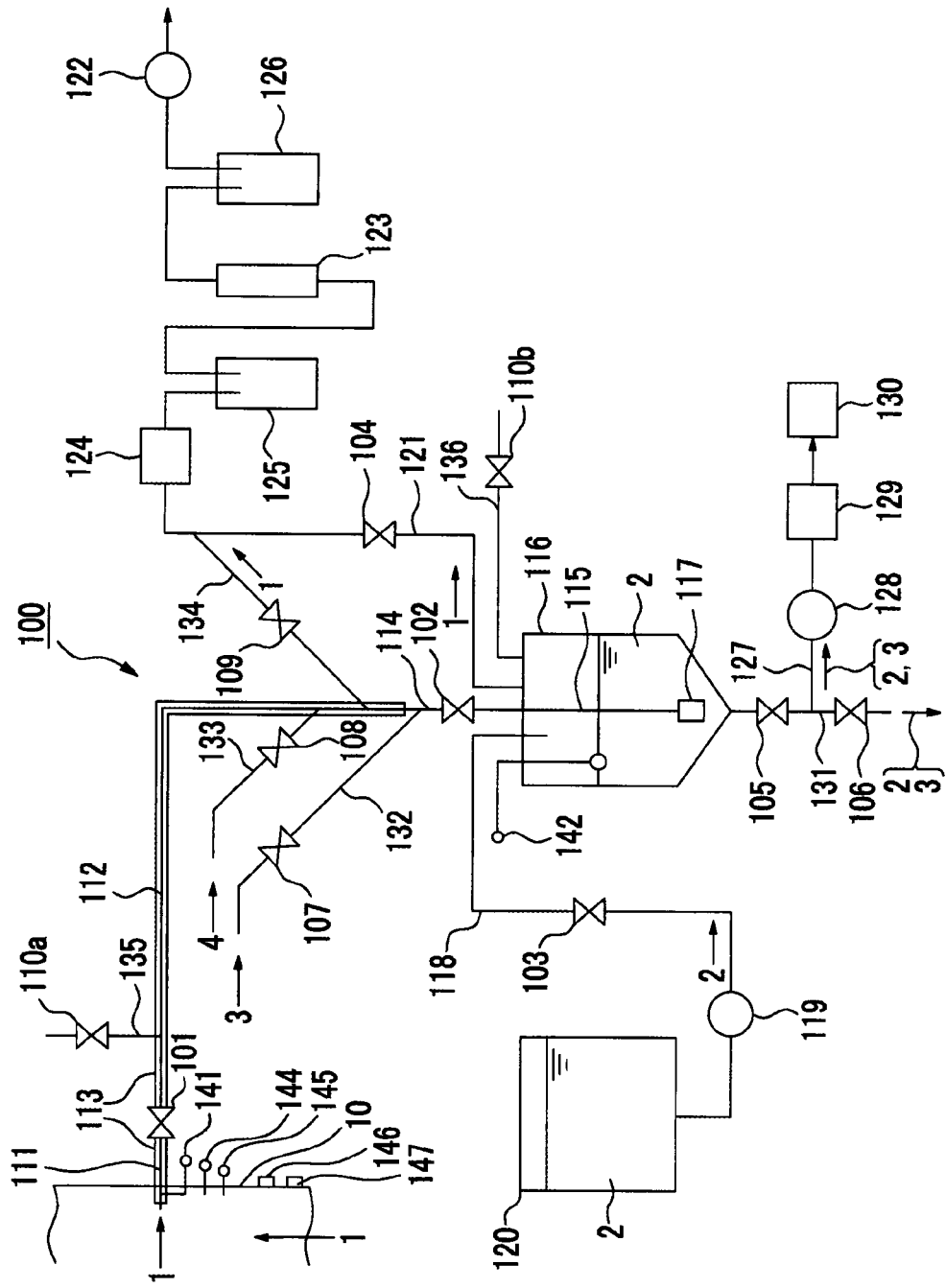
FIG. 1 is an overall schematic configuration view of a main embodiment of a mist-containing gas analysis device according to the present invention.

As illustrated in FIG. 1, a combustion exhaust gas 1 flows through a duct 10, and is a target gas which is brought into contact with amine-containing collection liquid and from which carbon dioxide is absorbed and removed. The combustion exhaust gas 1 contains amines and ammonia (hereinafter, referred to as "amines and the like), which are measurement-target substances, not only in a gaseous phase but also in a mist phase.

A sampling tube 111 is attached onto a circumferential surface of the duct 10 in such a manner that a distal end side of the sampling tube 111 is positioned inside the duct 10. One end side of a guide tube 112 is connected to a proximal end side of the sampling tube 111 via a valve 101. The other end side of the guide tube 112 is connected to one end side (an upper end side) of an introduction tube 114, the axis of which is vertically oriented. Each of the sampling tube 111, the guide tube 112 and the introduction tube 114 are provided with an electric heater 113 which is heating means. The electric heater 113 can heat the insides of the tubes 111, 112 and 114 to a temperature (approximately 150° C. to 200° C.) at which the amines and the like evaporate.

The other end side (a lower end side) of the introduction tube 114 is connected to one end side of a feeding tube 115 via a valve 102. The feeding tube 115 is attached to a collection container 116 in such a manner that the other end side of the feeding tube 115 is positioned on a lower side inside the collection container 116. A filter 117 (the maximum pore size: 5 μm to 120 μm and in particular, 100 μm to 120 μm is preferable) is attached to the other end side of the feeding tube 115, and is microfine bubble forming means which is made of sintered glass.

The collection container 116 is connected to one end side of a delivery tube 118 that has a valve 103 and a feeding pump 119 in the middle thereof. The other end side of the delivery tube 118 is connected to a bottom portion of a liquid storage tank 120. Collection liquid 2 is stored in the liquid storage tank 120 to dissolve and collect the amines and the like.

That is, when the valve 103 is open and the feeding pump 119 operates, the collection liquid 2 in the liquid storage tank 120 can be supplied into the collection container 116 via the delivery tube 118.

An upper portion of the collection container 116 is connected to a proximal end side of an exhaust tube 121 that has a valve 104 and a suction blower 122 in the middle thereof. A gas flow meter 123 is provided between the valve 104 and the suction blower 122 of the exhaust tube 121, and is gas flow rate detecting means for detecting gas that flows through the exhaust tube 121. A cooler 124 and a gas-liquid separator 125 intervene between the valve 104 and the gas flow meter 123 of the exhaust tube 121. A buffer tank 126 intervenes between the gas flow meter 123 and the suction blower 122 of the exhaust tube 121.

A bottom portion of the collection container 116 is connected to one end side of a liquid feeding tube 127 that has a valve 105 in the middle thereof. The other end side of the liquid feeding tube 127 is connected to an inlet of a feeding pump 128. An outlet of the feeding pump 128 is connected to an inlet of a constant volume and dilution device 129 that takes a constant volume and performs dilution. An inlet of a measuring device 130 is connected to an outlet of the constant volume and dilution device 129, and is measuring means such as an ion exchange chromatography device or an electric conductivity measuring device for measuring a concentration of the amines and the like.

One end side of a liquid exhaust tube 131 having a valve 106 in the middle thereof is connected to between the valve 105 and the feeding pump 128 of the liquid feeding tube 127. The other end side of the liquid exhaust tube 131 is connected to the outside of the system.

One end side of a pure liquid introduction tube 132 having a valve 107 in the middle thereof is connected to the vicinity of the valve 102 on the other end side (the lower end side) of the introduction tube 114. The axis of the pure liquid introduction tube 132 is oriented to slope in such a manner that one end side of the pure liquid introduction tube 132 is positioned lower than the other end side thereof. The other end side of the pure liquid introduction tube 132 is connected to a pure liquid tank that feeds pure liquid 3 such as pure water and is not illustrated.

One end side of a nitrogen gas introduction tube 133 having a valve 108 in the middle thereof is connected to the vicinity of the connected portion between one end side (the upper end side) of the introduction tube 114 and the guide tube 112. The axis of the nitrogen gas introduction tube 133 is oriented to slope in such a manner that one end side of the nitrogen gas introduction tube 133 is positioned lower than the other end side thereof. The other end side of the nitrogen gas introduction tube 133 is connected to a nitrogen gas bombe that feeds nitrogen gas 4, which is an inert gas, and is not illustrated.

One end side of a bypass tube 134 having a valve 109 in the middle thereof is connected to between the portions in which the introduction tube 114 is connected to each of the pure liquid introduction tube 132 and the nitrogen gas introduction tube 133. The other end side of the bypass tube 134 is connected to between the valve 104 of the exhaust tube 121 and the cooler 124.

The guide tube 112 is connected to one end side of a leakage tube 135 that has a valve 110a in the middle thereof. The other end side of the leakage tube 135 is connected to the outside of the system. One end side of a leakage tube 136 having a valve 110b in the middle thereof is connected to the upper portion of the collection container 116. The other end side of the leakage tube 136 is connected to the outside of the system.

A temperature sensor 141 is provided on the distal end side of the sampling tube 111, and is temperature detecting means. A float-type liquid flow rate detector 142 is provided in the collection container 116, and is liquid flow rate detecting means for detecting a flow rate of the collection liquid 2 in the collection container 116.

Each of a temperature sensor 144, a pressure meter 145, a flow rate measuring instrument 146 and a gas composition measuring instrument 147 is attached onto the circumferential surface of the duct 10, and is positioned upstream of the attachment location of the sampling tube 111 in a flow-through direction of the combustion exhaust gas 1. For example, the temperature sensor 144 is a thermocouple, and is an instrument that measures a temperature of the combustion exhaust gas 1 which flows through the duct 10. For example, the pressure meter 145 is a pressure gauge, and is an instrument that measures a pressure of the combustion exhaust gas I which flows through the duct 10. For example, the flow rate measuring instrument 146 is a radio wave type flow meter or an ultrasonic wave type flow meter which uses the Doppler effect, and is an instrument that measures a flow rate of the combustion exhaust gas 1 without causing turbulence of the flow of the combustion exhaust gas 1 by irradiating a radio wave or an ultrasonic wave at a predetermined angle toward the combustion exhaust gas flowing through the duct 10, and by detecting a change in frequency of a reflected wave. For example, the gas composition measuring instrument 147 is an instrument that measures a composition (water content) of the combustion exhaust gas 1 by using infrared light without causing turbulence of flow of the combustion exhaust gas 1.

Figure 2:
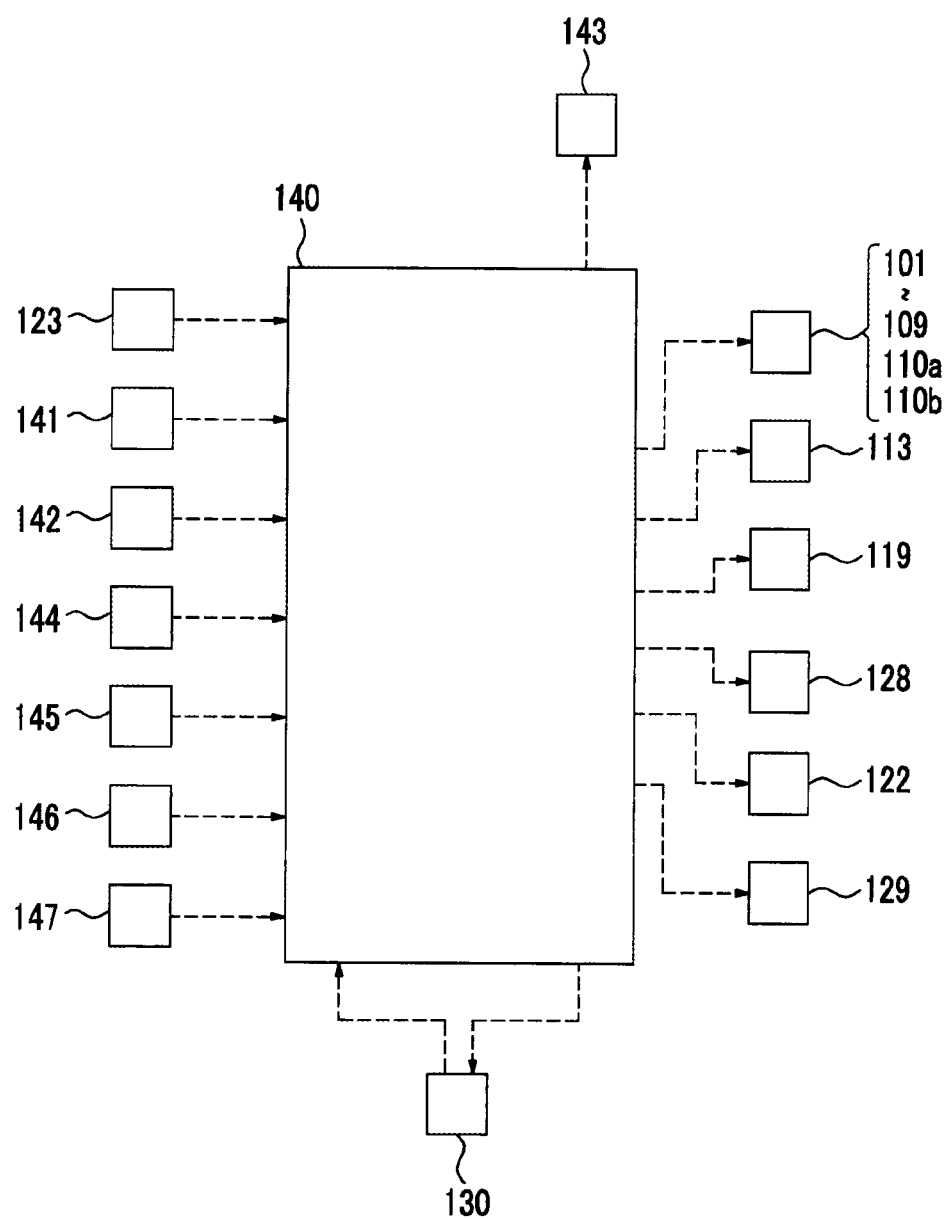
FIG. 2 is a block diagram of a control system of the mist-containing gas analysis device in FIG. 1.

As illustrated in FIG. 2, the gas flow meter 123, the temperature sensor 141, the flow rate detector 142, the temperature sensor 144, the pressure meter 145, the flow rate measuring instrument 146, and the gas composition measuring instrument 147 are electrically connected to an input unit of the arithmetic and control device 140 that is arithmetic and control means with a built-in timer. Furthermore, the measuring device 130 is electrically connected to the input unit of the arithmetic and control device 140. An output unit of the arithmetic and control device 140 is electrically connected to the valves 101 to 109, 110a and 110b, the electric heater 113, the feeding pumps 119 and 128, the suction blower 122, the constant volume and dilution device 129, and the measuring device 130, and the output unit of the arithmetic and control device 140 is electrically connected to a monitor 143 which is display means. Based on information from the gas flow meter 123, the temperature sensor 141, the flow rate detector 142, the temperature sensor 144, the pressure meter 145, the flow rate measuring instrument 146, the gas composition measuring instrument 147, and the timer, the arithmetic and control device 140 controls an operation of each of the valves 101-109, 110a and 110b, the electric heater 113, the feeding pumps 119 and 128, the suction blower 122, the constant volume and dilution device 129, and the measuring device 130. Based on information from the measuring device 130, the arithmetic and control device 140 can control the operation of the constant volume and dilution device 129, and can display various information on the monitor 143 (details will be described later).

In the embodiment, target gas sampling means is configured to have the valves 101, 102 and 104, the sampling tube 111, the guide tube 112, the introduction tube 114, the feeding tube 115, the collection container 116, the exhaust tube 121, the gas flow meter 123, the cooler 124, the gas-liquid separator 125, the buffer tank 126 and the like. Suction means is configured to have the suction blower 122 and the like. Target gas feeding means is configured to have the valves 102 and 104, the introduction tube 114, the feeding tube 115, the exhaust tube 121, the suction blower 122, the gas flow meter 123, the cooler 124, the gas-liquid separator 125, the buffer tank 126 and the like. Pure liquid supplying means is configured to have the vales 107, the pure liquid introduction tube 132, the pure liquid tank and the like. Liquid aliquot taking means is configured to have the valve 105, the liquid feeding tube 127, the feeding pump 128, the constant volume and dilution device 129 and the like. Collection liquid supplying means is configured to have the valve 103, the delivery tube 118, the feeding pump 119, the liquid storage tank 120 and the like. Liquid exhausting means is configured to have the valve 106, the liquid exhaust tube 131 and the Inert gas supplying means is configured to have the valve 108, the nitrogen gas introduction tube, the nitrogen gas bombe and the like. Bypass means is configured to have the valve 109, the bypass tube 134 and the like. Temperature measuring means is configured to have the temperature sensor 144 and the like. Pressure measuring means is configured to have the pressure meter 145 and the like. Flow rate measuring means is configured to have the flow rate measuring instrument 146 and the like. Water content measuring means is configured to have the gas composition measuring instrument 147 and the like.

Subsequently, an operation of the mist-containing gas analysis device 100 with this configuration according to the embodiment will be described.

Initially, all the valves 101 to 109 are closed. When the arithmetic and control device 140 operates, based on information from the temperature sensor 141, first, the arithmetic and control device 140 controls an operation of the electric heater 113 in such a manner that the tubes 111, 112 and 114 are heated to the temperature (approximately, 150° C. to 200° C.) at which the amines and the like evaporate.

Subsequently, based on information from the flow rate detector 142, the arithmetic and control device 140 controls an opening and closing of each of the valves 103 and 110b and an operation of the feeding pump 119 in such a manner that a specified flow rate of the collection liquid 2 is stored in the collection container 116. Accordingly, while gas in the collection container 116 is discharged to the outside of the system via the leakage tube 136, the collection liquid 2 in the liquid storage tank 120 is fed into the collection container 116 via the delivery tube 118.

When a specified flow rate of the collection liquid is stored in the collection container 116, based on information from the flow rate detector 142, the arithmetic and control device 140 controls each of the valves 101 and 109 to be open to purge insides of the sampling tube 111 and the guide tube 112 with the combustion exhaust gas 1 that flows through the duct 10, and the arithmetic and control device 140 controls an operation of the suction blower 122. Accordingly, the combustion exhaust gas 1 in the duct 10 is taken into the sampling tube 111, and is discharged to the outside of the system via the guide tube 112, the bypass tube 134 and then the exhaust tube 121.

In this way, when the insides of the sampling tube 111 and the guide tube 112 are purged with the combustion exhaust gas 1 for a predetermined time, based on information from the timer, the arithmetic and control device 140 controls the valve 109 to be closed (the valve 101 maintains the open state) to bring the combustion exhaust gas 1 into contact with the collection liquid 2 in the collection container 116, and the arithmetic and control device 140 controls the valves 102 and 104 to be open. Accordingly, the combustion exhaust gas 1 is fed into the collection liquid 2 in the collection container 116 via the feeding tube 115 and then the filter 117, and the amines and the like in the combustion exhaust gas 1 are dissolved and collected in the collection liquid 2. In contrast, the combustion exhaust gas 1, the amines and the like of which are collected in the collection liquid 2, is fed into the cooler 124 via the exhaust tube 121 and cooled down, water in the combustion exhaust gas condenses to be separated into gas and liquid in the gas-liquid separator 125, and then the combustion exhaust gas 1, water of which is removed, is discharged to the outside of the system via the buffer tank 126 and then the suction blower 122 while a flow rate of the combustion exhaust gas 1 is measured by the gas flow meter 123.

At this time, since the electric heater 113 heats the tubes 111, 112 and 114 to the temperature (approximately 150° C. to 200° C.) at which the amines and the like evaporate, and the tubes 111, 112 and 114 are retained at the temperature, a gaseous phase and a mist phase of the amines and the like contained in the combustion exhaust gas 1 taken in from the duct 10 do not condense to attach onto inner wall surfaces of the tubes 111, 112 and 114, and in an evaporated state, the combustion exhaust gas 1 can be fed up to the feeding tube 115.

Since the combustion exhaust gas 1 is fed into the collection liquid 2 from the feeding tube 115 via the filter 117, it is possible to transform the combustion exhaust gas 1 into microfine bubbles and to increase contact surfaces between the bubbles and the collection liquid 2. It is possible to efficiently collect the amines and the like in the combustion exhaust gas 1.

Furthermore, as illustrated in FIG. 3, the arithmetic and control device 140 acquires a measured temperature, pressure and flow rate of the combustion exhaust gas 1 and measured water content in the combustion exhaust gas 1, which are measured by the temperature sensor 144, the pressure meter 145, the flow rate measuring instrument 146 and the gas composition measuring instrument 147 (a first step S1). Subsequently, based on the measured temperature, pressure, flow rate and gas composition of the combustion exhaust gas 1, the arithmetic and control device 140 calculates a flow velocity of the combustion exhaust gas per a predetermined arithmetic expression, for example, per the following equation (1) (a second step S2). Subsequently, the arithmetic and control device 140 determines whether a current operating value, that is, a suction velocity of the combustion exhaust gas 1 being suctioned by the suction blower 122 is within a predetermined ratio with respect to the flow velocity of the combustion exhaust gas calculated based on the measured data, for example, whether the suction velocity of the combustion exhaust gas 1 is within ±10% of the flow velocity thereof (a third step S3). When the current operating value is within ±10% of the flow velocity of the combustion exhaust gas 1, a control process proceeds to a fourth step S4. When the current operating value exceeds ±10% of the flow velocity of the combustion exhaust gas 1, a control process proceeds to a fifth step S5. In the fourth step S4, the suction blower 122 continuously operates as it is, and the control of the suction blower 122 is finished. In the fifth step S5, the suction blower 122 is adjusted in such a manner that a suction flow rate of the combustion exhaust gas 1 being suctioned by the suction blower 122 is within ±10% of the flow velocity of the combustion exhaust gas 1, and the control process proceeds to a sixth step S6. In the sixth step S6, the suction flow rate of the combustion exhaust gas 1 being suctioned by the suction blower 122 is the same as the flow velocity of the combustion exhaust gas 1, the gas suction is performed at a velocity equal to the flow velocity of the combustion exhaust gas 1, and the control of the suction blower 122 is finished.

[Equation 1]

$$V = \sqrt{\frac{2gh}{\gamma}} \quad (1)$$

V: flow velocity of combustion exhaust gas, g: gravitational acceleration 9.8 m/s$^2$, h: pressure In this way, when the combustion exhaust gas 1 of a specified integrated flow rate flows through the collection liquid 2 in the collection container 116, based on information from the gas flow meter 123, the arithmetic and control device 140 controls the valves 101, 102 and 104 to be closed in such a manner that the combustion exhaust gas 1 is not supplied into the collection liquid 2. After the suction blower 122 is controlled to stop operating, based on information from the timer, the arithmetic and control device 140 controls an opening and closing of each of the valves 107 and 110a in such a manner that the pure liquid 3 is fed into the introduction tube 114 via the pure liquid introduction tube 132 for a specified interval (at a specified flow rate), and the introduction tube 114 is filled with the pure liquid 3.

Subsequently, based on information from the timer, the arithmetic and control device 140 controls an opening and closing of each of the valves 102, 108 and 110b at a specified time in such a manner that the amines and the like attached onto the inner wall surface of the feeding tube 115 are fed into the collection container 116. The pure liquid 3 in the introduction tube 114 is pushed out by the nitrogen gas 4 out of the nitrogen gas introduction tube 133. The pure liquid 3 flows downward while being in contact with the inner wall surface of the feeding tube 115 in such a manner that the pure liquid 3 is in contact with all the amines and the like which are attached onto the inner wall surface of the feeding tube 115. The pure liquid 3 flows into the collection liquid 2 in the collection container 116 while exhausting the combustion exhaust gas 1 in the collection container 116 to the outside of the system via the leakage tube 136.

Accordingly, it is possible to collect all the amines and the like attached onto the inner wall surface of the feeding tube 115 in the collection container 116.

Subsequently, based on information from the timer, in such a manner that aliquots of the liquid 2 and 3 in the collection container 116 are partially taken by the constant volume and dilution device 129, the arithmetic and control device 140 controls an opening and closing of each of the valves 102, 105 and 108 and controls an operation of the feeding pump 128 at a specified time. While the nitrogen gas 4 is supplied into the collection container 116 via the nitrogen gas introduction tube 133, the introduction tube 114 and then the feeding tube 115, the liquid 2 and 3 in the collection container 116 are mixed and supplied to the constant volume and dilution device 129 via the liquid feeding tube 127 and then the feeding pump 128.

The arithmetic and control device 140 controls an operation of the constant volume and dilution device 129 in such a manner that a specified flow rate of the mixed liquid 2 and 3 is fed into the measuring device 130. When the measuring device 130 measures concentrations of the amines and the like in a constant volume of the liquid 2 and 3, based on information from the measuring device 130, the arithmetic and control device 140 determines whether the measured result is within a calibratable range. When the measured result is within the calibratable range, the arithmetic and control device 140 calculates the concentrations of the amines and the like in the combustion exhaust gas 1, and displays the result on the monitor 143.

In contrast, when the measured result of the measuring device 130 is out of the calibratable range, the arithmetic and control device 140 calculates a dilution rate at which the concentrations of the amines and the like in the liquid 2 and 3 supplied to the measuring device 130 are brought into within the calibratable range. The arithmetic and control device 140 controls an operation of the constant volume and dilution device 129 in such a manner that the liquid 2 and 3 is diluted with dilution liquid such as pure water at the calculated rate. When the constant volume and dilution device 129 dilutes the liquid 2 and 3 at the calculated rate, the arithmetic and control device 140 controls an operation of the constant volume and dilution device 129 in such a manner that a specified flow rate of the diluted liquid 2 and 3 is newly fed into the measuring device 130. The measuring device 130 newly measures concentrations of the amines and the like in the liquid 2 and 3. Based on information from the measuring device 130, the arithmetic and control device 140 calculates concentrations of the amines and the like in the combustion exhaust gas 1, and displays the result on the monitor 143.

In this way, when the concentrations of the amines and the like in the combustion exhaust gas 1 are acquired, based on information from the measuring device 130, the arithmetic and control device 140 controls the valves 102, 105, 106 and 108 to be open in such a manner that the liquid 2 and 3 in the collection container 116 are discharged to the outside of the system. While the nitrogen gas 4 is fed into the collection container 116 via the nitrogen gas introduction tube 133, the introduction tube 114 and then the feeding tube 115, all the liquid 2 and 3 in the collection container 116 are discharged to the outside of the system via the liquid feeding tube 127 and then the liquid exhaust tube 131.

In this way, when the liquid 2 and 3 are discharged to the outside of the system from the collection container 116 for a specified interval, based on information from the timer, in such a manner that the collection container 116 is filled with the pure liquid 3, the arithmetic and control device 140 controls the valves 105, 106 and 108 to be closed (the valve 102 maintains the open state), and controls the valves 107 and 110b to be open. The pure liquid 3 is supplied into the collection container 116 via the pure liquid introduction tube 132 and then the feeding tube 115 for a specified time. To the extent that the pure liquid 3 overflows from the leakage tube 136, the pure liquid 3 is supplied into the collection container 116 while supplying the pure liquid 3 into the collection container 116 via the pure liquid introduction tube 132 and then the feeding tube 115 for a specified interval and expelling gas in the collection container 116 to the outside of the system via the leakage tube 136.

In this way, when the pure liquid 3 is supplied into the collection container 116 for a specified interval (at a specified flow rate), based on information from the timer, in such a manner that the pure liquid 3 in the collection container 116 is discharged to the outside of the system, the arithmetic and control device 140 controls the valves 107 and 110b to be closed (the valve 102 maintains the open state), and controls the valves 105, 106 and 108 to be open. While the nitrogen gas 4 is fed into the collection container 116 via the nitrogen gas introduction tube 133, the introduction tube 114 and then the feeding tube 115, all the pure liquid 3 in the collection container 116 is discharged to the outside of the system via the liquid feeding tube 127 and then the liquid exhaust tube 131.

In this way, when the pure liquid 3 is discharged to the outside of the system from the collection container 116 for a specified interval, based on information from the timer, in such a manner that the filter 117 is cleaned, the arithmetic and control device 140 controls the valve 108 to be closed (each of the valves 102, 105 and 106 maintains the open state), and controls the valves 107 to be open. The pure liquid 3 is fed to the filter 117 via the pure liquid introduction tube 132 and then the feeding tube 115 for a specified interval to clean the filter 117, and the pure liquid 3 is discharged to the outside of the system via the liquid feeding tube 127 and then the liquid exhaust tube 131.

In this way, when the cleaning is performed by using the pure liquid 3 for a specified interval, based on information from the timer, the arithmetic and control device 140 controls the valves 102, 105, 106 and 107 to be closed, and the system returns to the initial state.

Hereinafter, when the operations described above are repeated, it is possible to automatically and continuously measure concentrations of the amines and the like in the combustion exhaust gas 1 that flows through the duct 10.

Accordingly, the mist-containing gas analysis device 100 according to the embodiment measures a gas flow rate, a pressure, a temperature and water content of the combustion exhaust gas 1 in the duct 10 without causing turbulence of a flow of the combustion exhaust gas 1, and calculates a flow velocity of the combustion exhaust gas 1 in the duct 10 based on the measured results. The mist-containing gas analysis device 100 controls the suction blower 122 in such a manner that a suction velocity of the combustion exhaust gas 1 being suctioned by the suction blower 122 is within a predetermined ratio with respect to a flow velocity of the combustion exhaust gas 1. Accordingly, it is possible to appropriately suck the combustion exhaust gas in the duct 10 at a velocity equal to the flow velocity of the combustion exhaust gas 1 without causing clogging which results from a change in properties of the combustion exhaust gas 1. Therefore, even though the combustion exhaust gas 1 contains the amines and the like not only in a gaseous phase but also in a mist phase, the mist-containing gas analysis device 100 can simply and accurately measure the concentration of the measurement-target substance in the combustion exhaust gas Other Embodiments In the exhaust gas processing device equipped with the carbon dioxide recovery device that recovers carbon dioxide in a combustion exhaust gas from a boiler or the like by bringing the combustion exhaust gas into contact with amine-containing absorbing liquid and by absorbing the carbon dioxide in the combustion exhaust gas with the absorbing liquid, the embodiment describes a case where concentrations of the amines and the like in the combustion exhaust gas 1 are measured. However, the present invention is not limited to the embodiment. For example, in a case where a device measures a concentration of a measurement-target substance in a target gas that contains a mist of the measurement-target substance, for example, in a case where the device measures a concentration of a liquid component in outlet gas (for example, a water saturation gas) of a gas-liquid contact device, the present invention is applicable similarly to in the embodiment.

INDUSTRIAL APPLICABILITY

Even though the target gas contains the measurement-target substance not only in a gaseous phase but also in a mist phase, the mist-containing gas analysis device according to the present invention can simply and accurately measure a concentration of the measurement-target substance in the target gas. Accordingly, the present invention is very useful and is applicable to various industries.

REFERENCE SIGNS LIST

1: combustion exhaust gas
2: collection liquid
3: pure liquid
4: nitrogen gas
10: duct
100: mist-containing gas analysis device
101-109, 110a, 110b: valve
111: sampling tube
112: guide tube
113: electric heater
114: introduction tube
115: feeding tube
116: collection container
117: filter
118: delivery tube
119: feeding pump
120: liquid storage tank
121: exhaust tube
122: suction blower
123: gas flow meter
124: cooler
125: gas-liquid separator
126: buffer tank
127: liquid feeding tube
128: feeding pump
129: constant volume and dilution device
130: measuring device
131: liquid exhaust tube
132: pure liquid introduction tube
133: nitrogen gas introduction tube
134: bypass tube
135, 136: leakage tube
140: arithmetic and control device
141: temperature sensor
142: flow rate detector
143: monitor
144: temperature sensor
145: pressure meter
146: flow rate measuring instrument
147: gas composition measuring instrument

The invention claimed is:

1. A mist-containing gas analysis device that measures a concentration of a measurement-target substance in a target gas which contains a mist of the measurement-target substance flowing through a duct, the device comprising:
   pressure measuring means for measuring a pressure of the target gas that flows through the duct;
   temperature measuring means for measuring a temperature of the target gas that flows through the duct;
   flow rate measuring means for measuring a flow rate of the target gas that flows through the duct by using a radio wave or an ultrasonic wave;
   water content measuring means for measuring water content in the target gas that flows through the duct by using infrared light;
   a collection container that contains collection liquid which dissolves the measurement-target substance;
   target gas sampling means for absorbing the target gas by using suction means and for sampling the target gas;
   target gas feeding means for feeding the target gas sampled by the target gas sampling means into the collection liquid in the collection container;
   suction flow rate control means for controlling the suction means in such a manner that a suction velocity of the target gas being suctioned by the suction means is within a predetermined ratio with respect to a target gas flow velocity calculated based on the pressure of the target gas measured by the pressure measuring means, the temperature of the target gas measured by the temperature measuring means, the flow rate of the target gas measured by the flow rate measuring means, and the water content of the target gas measured by the water content measuring means;
   liquid aliquot taking means for taking an aliquot of the liquid in the collection container; and
   measuring means for measuring the concentration of the measurement-target substance in the aliquot of the liquid taken by the liquid aliquot taking means.

2. The mist-containing gas analysis device according to claim 1,
   wherein the measurement-target substances are amines and ammonia.

3. The mist-containing gas analysis device according to claim 2,
   wherein the target gas is a combustion exhaust gas from which carbon dioxide is absorbed and removed by the amine-containing absorbing liquid.

* * * * *